(12) United States Patent
Gwak et al.

(10) Patent No.: US 8,809,541 B2
(45) Date of Patent: Aug. 19, 2014

(54) HETEROCYCLIC COMPOUND, AND COMPOSITION FOR TREATING INFLAMMATORY DISEASES USING SAME

(75) Inventors: Hyung Sub Gwak, Daejeon (KR); Yong Zu Kim, Daejeon (KR); Uk Il Kim, Daejeon (KR); Byeong Deog Park, Daejeon (KR); Tae Kyo Park, Daejeon (KR); Sung Ho Woo, Daejeon (KR); Joung Yul Yun, Daejeon (KR); Dae Yon Lee, Daejeon (KR); Hyang Sook Lee, Daejeon (KR); Jeong Eun Jeon, Daejeon (KR); Se Kyoo Jeong, Daejeon (KR); Hyung Mook Choi, Daejeon (KR)

(73) Assignee: Neopharm Co., Ltd., Daejeon (KR)

( * ) Notice: Subject to any disclaimer, the term of this patent is extended or adjusted under 35 U.S.C. 154(b) by 0 days.

(21) Appl. No.: 13/818,355

(22) PCT Filed: Aug. 25, 2011

(86) PCT No.: PCT/KR2011/006281
§ 371 (c)(1),
(2), (4) Date: Mar. 8, 2013

(87) PCT Pub. No.: WO2012/026766
PCT Pub. Date: Mar. 1, 2012

(65) Prior Publication Data
US 2013/0158047 A1    Jun. 20, 2013

(30) Foreign Application Priority Data

Aug. 25, 2010 (KR) .................... 10-2010-0082258

(51) Int. Cl.
| | | |
|---|---|---|
| *A61K 31/497* | (2006.01) | |
| *C07D 211/32* | (2006.01) | |
| *A61Q 19/00* | (2006.01) | |
| *A61K 8/49* | (2006.01) | |
| *C07D 471/04* | (2006.01) | |
| *C07D 235/08* | (2006.01) | |

(52) U.S. Cl.
CPC ............. *C07D 235/08* (2013.01); *A61Q 19/00* (2013.01); *A61K 8/4946* (2013.01); *C07D 471/04* (2013.01)
USPC ..................................... 546/199; 514/254.06

(58) Field of Classification Search
None
See application file for complete search history.

(56) References Cited

U.S. PATENT DOCUMENTS 6,130,235 A * 10/2000 Mavunkel et al. ............ 514/322

FOREIGN PATENT DOCUMENTS

| EP | 1988076 A1 | 11/2008 |
|---|---|---|
| WO | 04/000817 A3 | 12/2003 |
| WO | 2007/043653 A1 | 4/2007 |
| WO | 2009/000413 A1 | 12/2008 |
| WO | 2010/012745 A3 | 2/2010 |

OTHER PUBLICATIONS

CAPLUS 1996:323082.*
Daniel Page et al., "Novel benzimidazole derivatives as selective CB2 agonists", Bioorganic & Medicinal Chemistry Letters, 2008, pp. 3695-3700, vol. 18.
Elena Cichero et al., "CoMFA and CoMSIA analyses on 1,2,3,4-tetrahydropyrrolo[3,4-b]indole and benzimidazole derivatives as selective CB2 receptor agonists", Journal of Molecular Modeling, Jan. 2010, pp. 1481-1498.
Hakan Goker et al., "Synthesis of some new benzimidazolecarboxamides and evaluation of their antimicrobial activity", Il Farmaco, 1998, pp. 415-420, vol. 53.
Leila Malik et al., "Discovery of non-peptidergic MrgX1 and MrgX2 receptor agonists and exploration of an initial SAR using solid-phase synthesis", Bioorganic & Medicinal Chemistry Letters, 2009, pp. 1729-1732, vol. 19.
International Searching Authority International Search Report for PCT/KR2011/006281 dated Apr. 17, 2012.
White et al., "The Synthesis and Chemiluminescence of an Amino Derivative and a Sulfur Analog of Luminol", The Journal of Organic Chemistry, Jun. 1967, vol. 32, Issue 6, pp. 1921-1926.
Curini et al., "Ytterbium Triflate Promoted Synthesis of Benzimidazole Derivatives", Synlett, 2004, No. 10, pp. 1832-1834, DOI: 10.1055/s-2004-829555, Art ID: G09204ST.
Yagupolskii et al., "2-Alkyl-1-(2-aryl-1, 1-difluoro-2-hydroxyethyl)benzimidazoles: potential angiotensin II receptor antagonists", Tetrahedron Letters, Elsevier Science Ltd., Mar. 27, 2000, vol. 41, Issue 13, pp. 2265-2267.
Schulenberg et al., "The Preparation of 2-Methyl-1-phenylbenzimidazole 3-Oxide", The Journal of Organic Chemistry, Apr. 1965, vol. 30, Issue 4, pp. 1279-1281, DOI: 10.1021/jo01015a529.
Iemura et al., "Synthesis of 2-(4-Substituted-1-piperazinyl)benzimidazoles as H1-Antihistaminic Agents", Journal of Medicinal Chemistry, American Chemical Society, Jul. 1986, vol. 29, Issue 7, pp. 1178-1183.
Page et al., "Novel benzimidazole derivatives as selective CB2 agonists", Bioorganic & Medicinal Chemistry Letters, Elsevier Ltd., Jul. 1, 2008, vol. 18, Issue 13, pp. 3695-3700.

(Continued)

*Primary Examiner* — Heidi Reese
(74) *Attorney, Agent, or Firm* — Sughrue Mion, PLLC

(57) ABSTRACT

Provided are heterocyclic compounds, having effects of treating and preventing inflammatory diseases and treating skin wounds, and particularly, exhibiting effects of recovering disrupted skin barriers, mitigating inflammation, and pruritus. Also, a composition containing the compound as an effective component can be used to mitigate various inflammatory diseases and protease activated receptor-2 (PAR-2)-overexpressed diseases, and can be particularly used as a composition having an anti-inflammatory function in inflammatory skin diseases including atopic dermatitis and the like, by inhibiting PAR-2 activity.

10 Claims, 4 Drawing Sheets

(56) References Cited

OTHER PUBLICATIONS

Cichero et al., "CoMFA and CoMSIA analyses on 1,2,3,4-tetrahydropyrrolo[3,4-b]indole and benzimidazole derivatives as selective CB2 receptor agonists", Journal of Molecular Modeling, Sep. 2010, vol. 16, Issue 9, pp. 1481-1498, DOI: 10.1007/s00894-010-0664-1.

Goker et al., "Synthesis of some new benzimidazolecarboxamides and evaluation of their antimicrobial activity", Il Farmaco, Elsevier Science S.A., Jun. 30, 1998, vol. 53, Issue 6, pp. 415-420.

Database Registry [Online] Chemical Abstracts Service, Columbus, Ohio, US; Sep. 16, 2002, XP002717820, Database accession No. 451497-56-6, compound with the Registry No. 451497-56-6.

Database Registry [Online] Chemical Abstracts Service, Columbus, Ohio, US; Dec. 26, 2008, XP002717821, Database accession No. 1090379-07-9, compound with the Registry No. 1090379-07-9.

Database Registry [Online] Chemical Abstracts Service, Columbus, Ohio, US; Sep. 17, 2002, XP002717851, Database accession No. 452079-19-5 X 1-4, compound with the Registry No. 452079-19-5.

Database Registry [Online] Chemical Abstracts Service, Columbus, Ohio, US; Mar. 31, 2006, XP002717852, Database accession No. 878666-39-8, compound with the Registry No. 878666-39-8.

Database Registry [Online] Chemical Abstracts Service, Columbus, Ohio, US; May 19, 2009, XP002717853, Database accession No. 1147287-43-1, compound with the Registry No. 1147287-43-1.

Database Registry [Online] Chemical Abstracts Service, Columbus, Ohio, US; Sep. 7, 2009, XP002717854, Database accession No. 1180984-39-7, compound with the Registry No. 1180984-39-7.

Database Registry [Online] Chemical Abstracts Service, Columbus, Ohio, US; Sep. 11, 2009, XP002717855, Database accession No. 1182590-22-2, compound with the Registry No. 1182590-22-2.

European Patent Office, Communication dated Jan. 14, 2014, issued in corresponding European Application No. 11820193.8.

\* cited by examiner

Skin surface hydration in Oxazolone model

PCNA-positive keratinocyte in Oxazolone model

***: p<0.001 versus vehicle treated group. P value was calculated by student's t-test.

\*\*: p<0.01 versus vehicle treated group. P value was calculated by student's t-test.

HETEROCYCLIC COMPOUND, AND COMPOSITION FOR TREATING INFLAMMATORY DISEASES USING SAME

CROSS REFERENCE TO RELATED APPLICATIONS

This application is a National Stage of International Application No. PCT/KR2011/006281 filed Aug. 25, 2011, claiming priority based on Korean Patent Application No. 10-2010-0082258 filed Aug. 25, 2010, the contents of all of which are incorporated herein by reference in their entirety.

TECHNICAL FIELD

The present invention relates to compounds including benzoimidazole derivatives and salts thereof, as new heterocyclic compounds, and more particularly to, a protease activated receptor-2 (PAR-2) inhibitor and a composition for treating and preventing inflammatory diseases.

BACKGROUND ART

Protease activated receptor-2 (PAR-2) belongs to G-protein-coupled receptor (GPCR), and was found in association with thrombin receptor (PAR-1) found in 1991. As the results of searching PAR-2 activation mechanism, the PAR-2 has been known to have a specific activation mechanism in that when a protease, such as trypsin or cell-derived tryptase, cleaves a specific site of a peptide sequence present at a terminal of an extracellular domain of the PAR-2, a peptide sequence appearing at a terminal of the receptor (for example, SLIGRL for human) is combined with a specific site of the PAR-2, which is then activated (Exp. Rev. Mol. Med. 4(16): 1-17, 2002).

It has been recently reported that the PAR-2 plays an important role in skin inflammation reaction, skin barrier function, and pruritus occurrence, and thereby a strong association between the role of the PAR-2 and atopic dermatitis showing all those symptoms as major disease symptoms are represented.

PAR-2 has been known to be exhibited in various cells of human, and has been reported to be effective in inducing inflammatory reactions, activation reactions of nerve cells, and the like. Also, it has been reported that the PAR-2 promotes transport of melanosome while being involved in signal transmission mechanism between keratinocyte and melanocyte in the skin, and thus is closely associated with pigmentation of the skin (Drug Dev. Res. 59: 408-416, 2003).

In addition, it has been recently reported that activation of the PAR-2 is very closely associated with the skin barrier function. That is, it has been reported that, when the skin barrier function is damaged, the activity of protease rapidly increase in the stratum corneum, which leads to activation of the PAR-2 (J. Invest Dermatol 126: 2074-2076, 2006), and it has been confirmed that a house dust mite- or roach-derived material, which is a kind of allergen, causing and exacerbating atopic dermatitis, also has an effect of activating the PAR-2. Previous studies of the present researcher showed that, when allergen is applied to the skin having disrupted skin barriers, the activation of PAR-2 inhibits the recovery of the skin barrier function, and when a PAR-2 inhibitor and allergen are simultaneously applied, the barrier recovery mechanism is normalized (J. Invest. Dermatol. 128: 1930-1939, 2008). Also, it was reported that the recovery of the skin barrier is promoted when the PAR-2 inhibitor is applied to the skin having disrupted skin barriers. In consideration that the skin barrier disruption is the most common symptom in the skin of patients with atopic dermatitis, this effect of the PAR-2 inhibitor of recovering disruption of the skin barrier is expected to be capable of helping improve the symptoms of atopic dermatitis.

It has been reported that intradermal activation of the PAR-2 causes pruritus, and it has been known that this pruritus causes scratching behavior. According to the existing research results on anti-pruritic effects of PAR-2 inhibitors (Japanese Patent Laid-Open Publication No. JP2004-170323), it has been reported that scratching behavior was significantly reduced when the PAR-2 inhibitor was applied to the skin. According to the known pruritic mechanism, nerve cells are activated by activation of PAR-2 present in the nerve fiber in the skin, and thus a signal of pruritic is transmitted to the brain. It was confirmed that, in an animal model where a PAR-2 activating material is applied to the skin, the function of PAR-2 associated with pruritic rapidly increased the number of times of scratching, and this phenomenon was suppressed when activation of the PAR-2 was inhibited (J. Neurosci. 2003, 23, 6176-6180).

As materials having a selective inhibitory efficiency to PAR-2, two species have been currently known all over the world, and one of them is ENMD-1,068 of EntreMed Company, a bio-venture company in the United States, of which efficacy was verified in an academic journal. Also, Japan Patent Laid-Open Publication No. 2004-170323 by Sumitomo Pharmacy Company discloses a PAR-2 inhibitor.

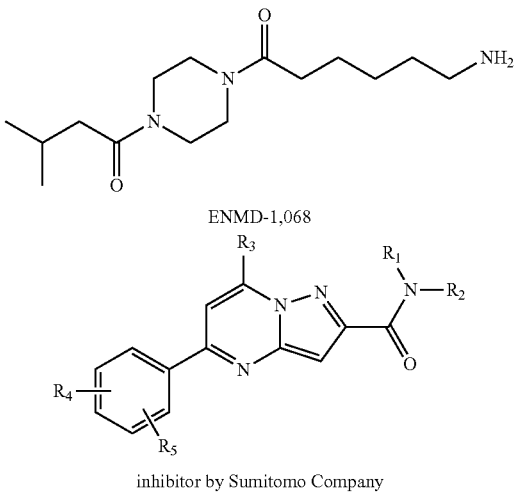

ENMD-1,068 inhibitor by Sumitomo Company

With respect to exacerbation of skin inflammation due to PAR-2 and anti-inflammatory effects of materials having PAR-2 inhibitory activity, it was confirmed that, when trypsin, which is a protease of activating PAR-2, or activating peptide (AP), which is a material of activating PAR-2, was applied to the skin, skin inflammation was increased, and when a protease inhibitor was together applied, the skin inflammation was reduced (FASEB J. 2003, 17, 1871-1885).

The present inventors synthesized various compounds for a long time in order to synthesize materials having PAR-2 inhibitory activity and confirmed activities thereof, and finally invented new compounds having excellent PAR-2 inhibitory activity.

DISCLOSURE

Technical Problem

An object of the present invention is to provide heterocyclic compounds represented by Chemical Formula 1 below, as new heterocyclic compounds.

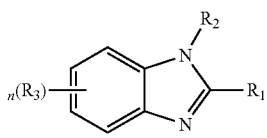
[Chemical Formula 1]

Another object of the present invention is to provide a pharmaceutical composition for treating and preventing inflammatory diseases, including the heterocyclic compound of Chemical Formula 1 according to the present invention or a pharmaceutically acceptable salt thereof, and also, a protease activated receptor-2 (PAR-2) inhibitor composition including the compound of Chemical Formula 1 or a pharmaceutically acceptable salt thereof.

Technical Solution

In one general aspect, there is provided a benzoimidazole compound represented by Chemical Formula 1 below, which is a new heterocyclic compound:

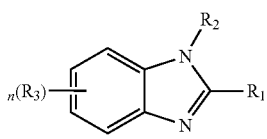
[Chemical Formula 1]

[in Chemical Formula 1, $R_1$ is selected from hydrogen, halogen, (C1-C7)alkyl, (C6-C12)aryl, (C3-C6)cycloalkyl, (C6-C12)ar(C1-C7)alkyl, and

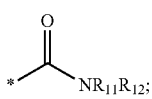

$R_2$ and $R_3$ each are independently selected from hydrogen, halogen, (C1-C7)alkyl, (C3-C6)cycloalkyl, (C6-C10)aryl, (C6-C10)ar(C1-C7)alkyl, (C1-C7)alkoxycarbonyl, (C1-C7)alkylamido(C1-C7)alkyl,

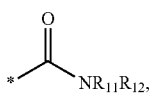

$-NR_{13}R_{14}$, and

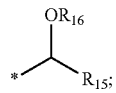

$R_{11}$, $R_{12}$, $R_{13}$, $R_{14}$, $R_{15}$ and $R_{16}$ each are independently hydrogen, (C1-C7)alkyl, (C3-C6)cycloalkyl, (C6-C10)aryl, heterocycloalkyl(C6-C12)aryl, or (C3-C12)heteroaryl, and $R_{11}$ and $R_{12}$ and $R_{14}$ and $R_{15}$ may be linked to each other via alkylene, oxyalkylene, or aminoalkylene to form a 5-membered or 6-membered hetero ring;

n is an integer of 1 to 4;

(C6-C12)aryl of R2 and R3 and the hetero ring formed from R11 and R12 may be further substituted with halogen, hydroxy, (C1-C7)alkyl, (C6-C10)aryl, (C3-C6)cycloalkyl, 5- or 6-membered heterocycloalkyl, 5- or 6-membered heterocycloalkylcarbonyl, 5- or 6-membered cycloalkyl sulfonyl, 5- or 6-membered heteroaryl, (C1-C6)alkoxy, (C1-C7)alkoxycarbonyl, (C1-C7)alkylcarbonyl, (C3-C6)cyclo(C1-C7)alkylcarbonyl, (C6-C10)ar(C1-C7)alkylcarbonyl, (C3-C10)heteroarylcarbonyl, (C6-C10)arylcarbonyl, (C1-C7)alkylsulfonyl, amino(C1-C7)alkylcarbonyl, (C1-C7)alkyloxycarbonyl, (C6-C10)ar(C1-C7)alkyloxycarbonyl, amino(C1-C7)alkylamino, (C1-C7)alkylamido, (C1-C7)alkylcarbamoyl, (C1-C7)alkylsulfoneamido, or

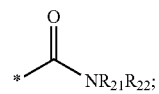

and $R_{21}$ and $R_{22}$ each are independently (C1-C7)alkyl, (C3-C6)cycloalkyl, or (C6-C12)aryl, or $R_{21}$ and $R_{22}$ may be linked to each other via alkylene to form a 5- or 6-membered hetero ring].

The term substituents including "alkyl", "alkoxy" and the other "alkyl" portions, described herein, may have both straight chain or branched chain. In the present invention, (C1-C7)alkyl include methyl, ethyl, n-propyl, i-propyl, n-butyl, i-butyl, t-butyl, n-pentyl, i-pentyl, n-hexyl, and n-heptyl; (C1-C6)alkoxy may include methoxy, ethoxy, n-propoxy, i-propoxy, n-butoxy, i-butoxy, t-butoxy, n-pentoxy, i-pentoxy, and n-hexyloxy; and (C3-C6)cycloalkyl may include cyclopropyl, cyclobutyl, cyclopentyl, and cyclohexyl. In addition, (C6-C12)aryl may include phenyl, naphthyl, biphenyl, anthryl, and the like. 5- or 6-membered hetero rings may include aliphatic hetero rings and hetero aryl. In particular, heterocycloalkyl, that is, aliphatic hetero rings may include morpholinyl, thiomorpholinyl, pyrrolidinyl, piperidinyl, piperazinyl, pyrrolidonyl, piperidonyl, oxazolidinonyl, and thiazolidinonyl; heteroaryl may include monocyclic heteroaryl such as furyl, thiophenyl, pyrrolyl, pyranyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, and the like, and polycyclic heteroaryl, such as, benzofuranyl, benzothiopenyl, isobenzofuranyl, benzoimidazolyl, benzothiadiazolyl, benzoisothiazolyl, benzoisoxazolyl, benzoxazolyl, isoindolyl, indolyl, indazolyl, benzothiazolyl, quinolyl, isoquinolyl, cinnolynyl, quinazolinyl, quinolizinyl, quinoxalinyl, carbazolyl, phenanthridinyl, benzodioxolyl, and the like.

More specifically, in Chemical Formula 1, $R_1$ is (C1-C7)alkyl;

$R_2$ is selected from hydrogen, halogen, (C1-C7)alkyl, (C6-C12)aryl, and (C6-C12)ar(C1-C7)alkyl;

$R_3$ is selected from hydrogen, halogen, (C1-C7)alkyl, (C6-C12)aryl, (C1-C7)alkoxycarbonyl, and;

$R_{11}$ and $R_{12}$ each are independently hydrogen, (C1-C7)alkyl, (C3-C6)cycloalkyl, (C6-C10)aryl, heterocycloalkyl(C6-C12)aryl, or (C3-C12)heteroaryl, and $R_{11}$ and $R_{12}$ may be linked to each other via alkylene, oxyalkylene, or aminoalkylene to form a 5- or 6-membered hetero ring;

n is an integer of 1 to 4;

the (C6-C12)aryl of $R_2$ and $R_3$ and the hetero ring formed from $R_{11}$ and $R_{12}$ may be further substituted with halogen, hydroxy, (C1-C7)alkyl, (C6-C10)aryl, (C3-C6)cycloalkyl, 5- or 6-membered heterocycloalkyl, 5- or 6-membered heterocycloalkylcarbonyl, 5- or 6-membered cycloalkyl sulfonyl, 5- or 6-membered heteroaryl, (C1-C6)alkoxy, (C1-C7)alkoxycarbonyl, (C1-C7)alkylcarbonyl, (C3-C6)cyclo(C1-C7)alkylcarbonyl, (C6-C10)ar(C1-C7)alkylcarbonyl, (C3-C10)heteroarylcarbonyl, (C6-C10)arylcarbonyl, (C1-C7)alkylsulfonyl, amino(C1-C7)alkylcarbonyl, (C1-C7)alkyloxycarbonyl, (C6-C10)ar(C1-C7)alkyloxycarbonyl, amino(C1-C7)alkylamino, (C1-C7)alkylamido, (C1-C7)alkylcarbamoyl, (C1-C7)alkylsulfoneamido, or

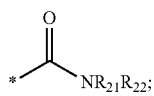

and $R_{21}$ and $R_{22}$ each are independently (C1-C7)alkyl, or (C3-C6)cycloalkyl, (C6-C12)aryl, or $R_{21}$ and $R_{22}$ may be linked to each other via alkylene to form 5- or 6-membered hetero rings.

More preferably, in the heterocyclic compound represented by Chemical Formula 1, $R_1$ is methyl; $R_2$ is benzyl or phenyl; $R_3$ is selected from (C1-C7)alkoxycarbonyl and

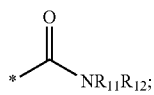

$R_{11}$ and $R_{12}$ each are independently hydrogen, (C1-C7)alkyl, (C3-C6)cycloalkyl, (C6-C10)aryl, heterocycloalkyl(C6-C12)aryl, or (C3-C12)heteroaryl; $R_{11}$ and $R_{12}$ may be linked to each other via alkylene, oxyalkylene, or aminoalkylene to form a 5- or 6-membered hetero ring; and n is an integer of 1 to 4.

In addition, the heterocyclic compound according to the present invention may include Chemical Formula 2 below:

[Chemical Formula 2]

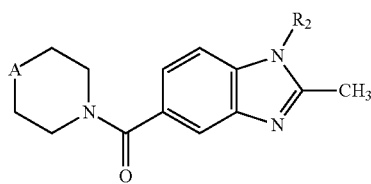

[in Chemical Formula 2,

A is $CH_2$ or $NR_{31}$;

$R_{31}$ is selected from hydrogen, (C1-C7)alkyl, (C1-C7)alkylcarbonyl, and (C3-C6)cycloalkylcarbonyl; and $R_2$ is benzyl or phenyl, and the benzyl or phenyl of $R_2$ may be further substituted with halogen, (C1-C7)alkyl, or 5- or 6-membered heterocycloalkyl].

Specific examples of the heterocyclic compound according to the present invention may be selected from the following structures, but are not limited thereto.

Compound 92

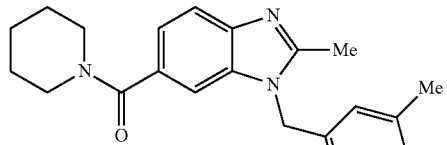

Compound 93

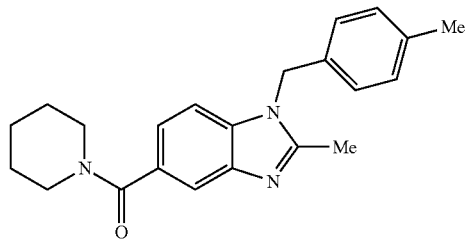

Compound 94

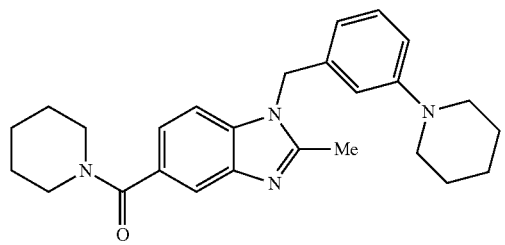

Compound 95

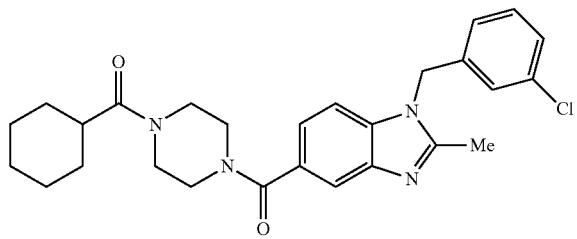

Compound 96

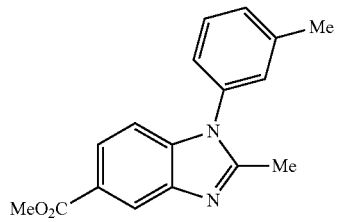

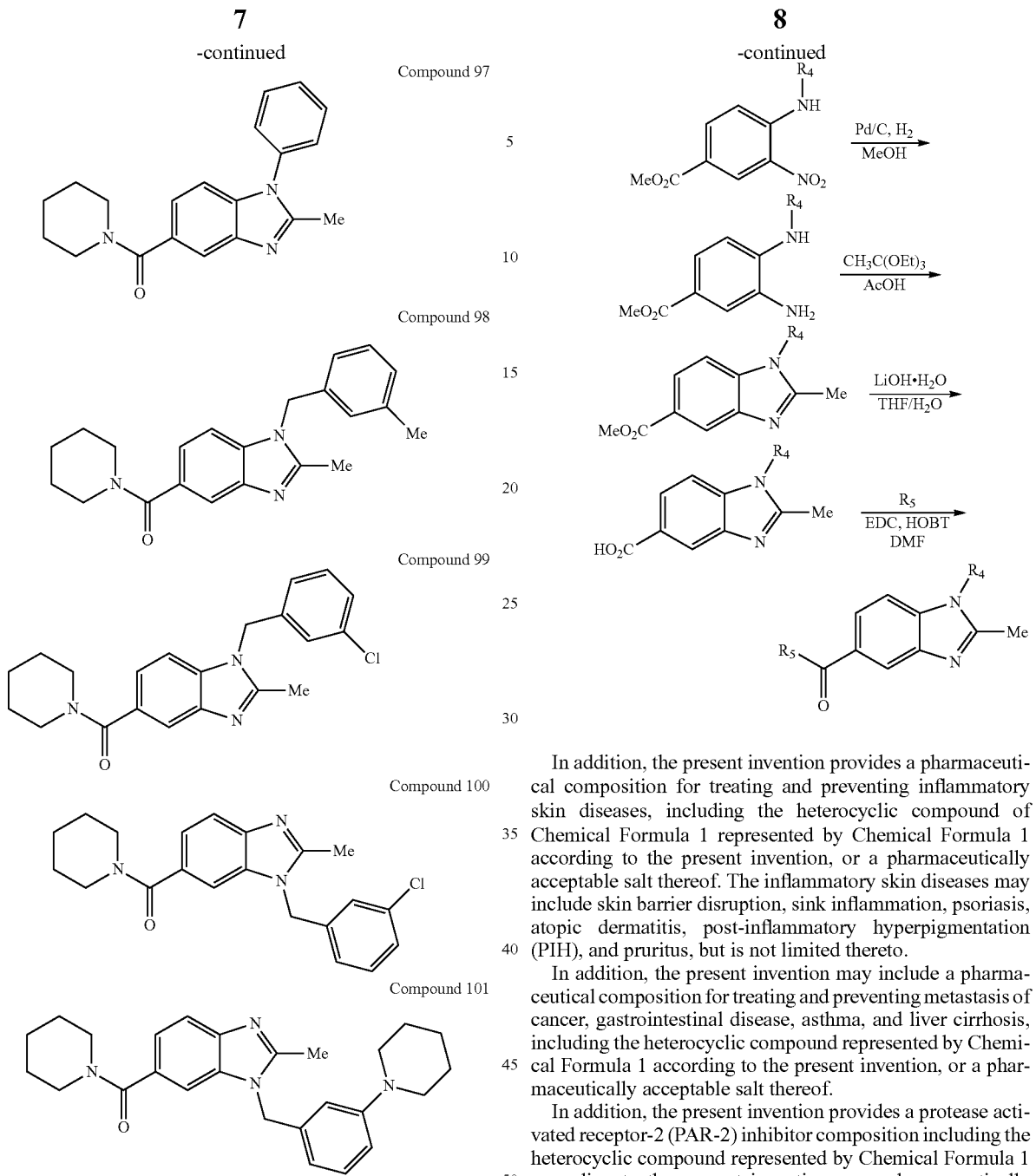

In addition, the present invention provides a pharmaceutical composition for treating and preventing inflammatory skin diseases, including the heterocyclic compound of Chemical Formula 1 represented by Chemical Formula 1 according to the present invention, or a pharmaceutically acceptable salt thereof. The inflammatory skin diseases may include skin barrier disruption, sink inflammation, psoriasis, atopic dermatitis, post-inflammatory hyperpigmentation (PIH), and pruritus, but is not limited thereto.

In addition, the present invention may include a pharmaceutical composition for treating and preventing metastasis of cancer, gastrointestinal disease, asthma, and liver cirrhosis, including the heterocyclic compound represented by Chemical Formula 1 according to the present invention, or a pharmaceutically acceptable salt thereof.

In addition, the present invention provides a protease activated receptor-2 (PAR-2) inhibitor composition including the heterocyclic compound represented by Chemical Formula 1 according to the present invention, or a pharmaceutically acceptable salt thereof.

In addition, the present invention provides a cosmetic composition including the heterocyclic compound represented by Chemical Formula 1 according to the present invention.

Advantageous Effects

The present invention provides heterocyclic compounds represented by Chemical Formula 1, and the compound of Chemical Formula 1 according to the present invention or the salt thereof is a protease activated receptor-2 (PAR-2) inhibitor and has high activity. PAR-2 has been known to play an important role in inflammation or cardiovascular diseases, cancer, particularly cancer metastasis, gastrointestinal diseases covering inflammatory Bowel disease (IBD) and the like, asthma, and live cirrhosis. As such, considering that the PAR-2 involved diseases are mainly intractable chronic dis- The compound of Chemical Formula 1 according to the present invention may be prepared by Reaction Scheme 1 below, but is not limited thereto.

[Reaction Scheme 1]

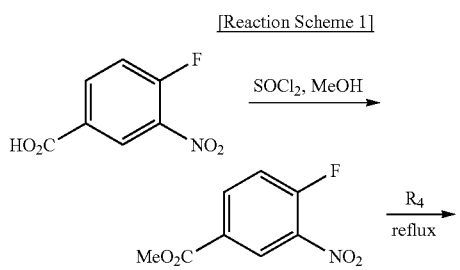

ease, development of effective PAR-2 inhibitors can be anticipated to have great commercial possibility.

In particular, as for the skin, it has been known that PAR-2 is involved in important reactions such as intradermal hyperpigmentation and pruritus induction in addition to inflammation, and, besides, it has been reported that PAR-2 plays important roles in maintaining the skin barrier function and treating the wounds, and thus the PAR-2 inhibitor also has high possibility in treating skin diseases. The atopic dermatitis, which is a skin disease simultaneously showing these various skin symptoms, is an intractable chronic inflammatory skin disease, and simultaneously shows various symptoms due to activation of PAR-2, such as severe pruritus and skin barrier disruption, post-inflammatory hyperpigmentation (PIH), and the like, and thus the atopic dermatitis is determined to be a disease to which the PAR-2 inhibitor is firstly applicable.

Further, it has been reported that the PAR-2 expression increases in a skin wound region, and it has been reported that when this wound region is treated with a component having PAR-2 inhibitory efficacy, treatment of the wound is promoted.

Therefore, the compound of Chemical Formula 1 or the salt thereof, according to the present invention, can be used for treating and preventing inflammatory diseases such as skin barrier disruption, skin inflammation, atopic dermatitis, and the like, and treating the wound, and is useful as a pharmaceutical composition or cosmetic composition.

Further, the compound of Chemical Formula 1 or the salt thereof, according to the present invention, is useful as a protease activated receptor-2 (PAR-2) inhibitor.

BEST MODE

Figure 1:
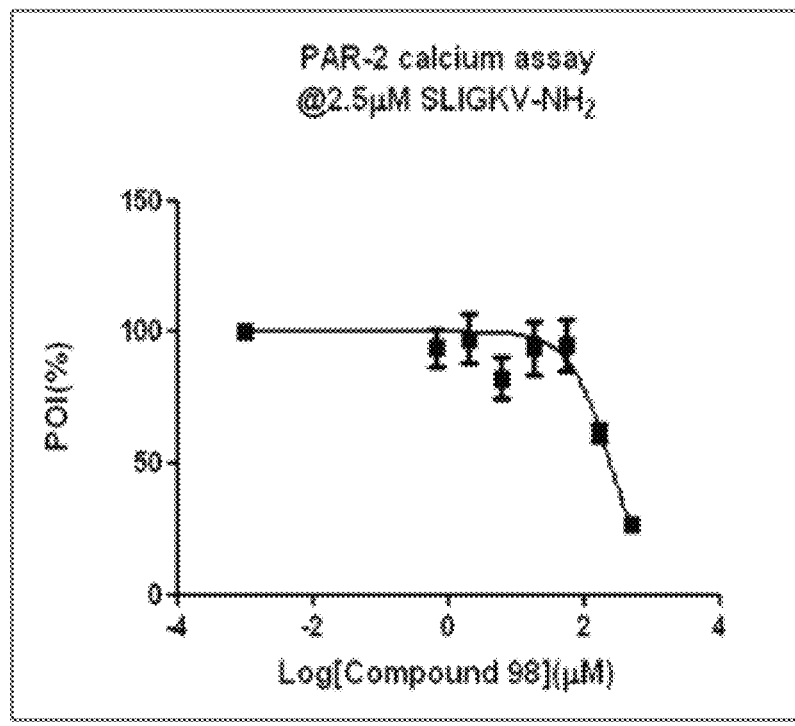
FIG. 1 shows a PAR-2 inhibitory activity assay profile, specified in Experimental Example 1.
Figure 2:
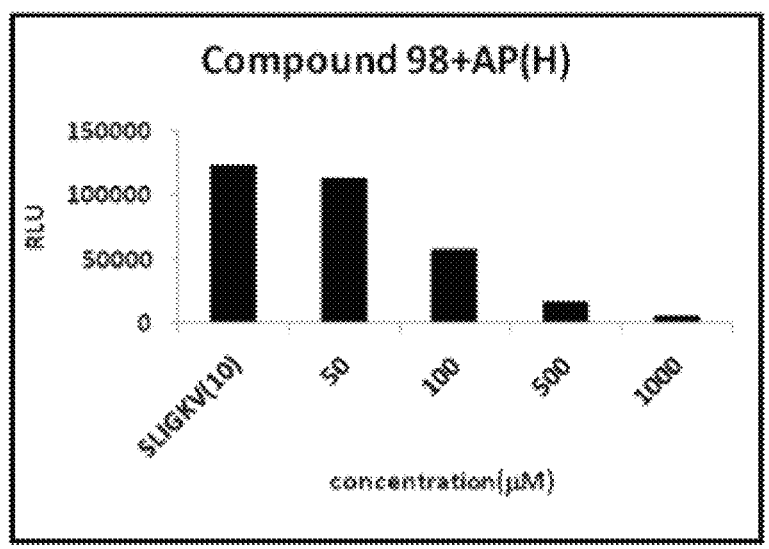
FIG. 2 shows β-arrestin assay results in Experimental Example 2.

The present invention is directed to providing heterocyclic compounds represented by Chemical Formula 1 below, as new heterocyclic compounds.

In order to evaluate PAR-2 inhibitory activity of the compound of Chemical Formula 1 according to the present invention, the mechanism of PAR-2 being known to be associated with treatment and prevention of inflammatory skin diseases, such as, skin barrier disruption, sink inflammation, psoriasis, Netherson syndrome, or atopic dermatitis, in vitro and in vivo experiments were conducted. As the results, it may be confirmed that the compound of the present invention had PAR-2 inhibitory activity in cells.

Accordingly, the present invention provides a pharmaceutical composition, a cosmetic composition, and a protease activated receptor-2 (PAR-2) inhibitor composition, for treating and preventing inflammatory skin diseases, including the compound of Chemical Formula 1 or the pharmaceutically acceptable salt thereof. Here, the inflammatory skin diseases include skin barrier disruption, psoriasis accompanied by sink inflammation, Netherson syndrome, atopic dermatitis, and the like.

In addition, the present invention may provide a pharmaceutical composition for treating skin wounds, using the fact that the suppression of PAR-2 expression promotes the treating of the wounds.

In the present invention, the pharmaceutical composition or the PAR-2 inhibitor composition may include, as an active ingredient, the compound of Chemical Formula 1 according to the present invention of 0.001-90 wt %, and preferably 0.001~50 wt %.

In addition, the pharmaceutical composition or the PAR-2 inhibitor composition for treating and preventing inflammatory skin diseases or treating skin wounds, according to the present invention, may include all the composition that may be administrable to the living body, including external applications, injections, inhalations, oral preparations, and the like. Dosage forms that are applicable to the skin or mucosa are not particularly limited, but may be formulated into liquid, liquid oil, suspension, cream, ointment, gel, jelly, or spray.

Hereinafter, the present invention will be described through the following examples and experimental examples, but the present invention is not limited to these examples.

Example 1

Preparation of (2-methyl-1-m-tolyl-1H-benzo[d] imidazol-5-yl)(piperidin-1-yl)methanone Compound 98

[Step 1] Preparation of methyl 4-fluoro-3-nitrobenzoate

4-Fluoro-3-nitrobenzoic acid (3.00 g, 16.2 mmol) was dissolved in methanol 40 mL, and thionyl chloride (3.5 mL, 48.6 mmol) was slowly added thereto at 0° C. The temperature was slowly raised to room temperature, and then stirred under reflux for 1 hour. The solvent was removed by concentration under reduced pressure, to obtain a target compound as an ivory solid (3.12 g, 97%).

$^1$H NMR (600 MHz, chloroform-d1) d=8.73 (dd, J=2.4 Hz, 7.5 Hz, 1H), 8.34 (m, 1H), 7.42 (t, J=9.0 Hz, 1H), 3.99 (s, 3H)

[Step 2] Preparation of methyl 3-amino-4-(m-tolylamino)benzoate

The compound obtained in Step 1 (1.30 g, 6.53 mmol), m-toluidine (1.40 g, 13.1 mmol), and potassium carbonate (870 mg, 6.53 mmol) were dissolved in acetonitrile, and then stirred under reflux for 12 hours. The solvent was removed by concentration under reduced pressure, and then the precipitate generated by adding hexane thereto was filtered and washed with hexane, to obtain methyl 3-nitro-4-(m-tolylamino)benzoate as an orange solid (1.37 g, 73%).

The above compound (1.00 g, 3.49 mmol) was dissolved in MeOH 50 mL, and then 50 mg of Pd/C was added thereto, followed by stirring under hydrogen gas of 1 atm for 2 hours. The reacted mixture was filtered by using celite, and the filtrate was concentrated under reduced pressure, to obtain a target compound as a yellow solid (0.90 g, 99%).

$^1$H NMR (600 MHz, chloroform-d1) d=7.46 (m, 2H), 7.13-7.15 (m, 2H), 6.74 (m, 3H), 5.59 (s, 1H), 3.85 (s, 3H), 3.65 (s, 2H), 2.29 (s, 3H)

[Step 3] Preparation of 2-methyl-1-m-tolyl-1H-benzo[d]imidazole-5-carboxylic acid A mixture of the compound obtained in Step 2 (0.46 g, 1.80 mmol) and triethyl orthoacetate (1.46 g, 9.00 mmol) was dissolved in 3 mL of acetic acid 3 mL, and stirred under reflux for 12 hours. The reacted mixture was cooled to room temperature and concentrated under reduced pressure, and then diluted with 20 mL of ethyl acetate. The resultant material was washed with 30 mL of a saturated aqueous solution of sodium carbonate twice and then 30 mL of water once, sequentially, and then the organic layer was taken, and dehydrated with anhydrous sodium sulfonate and concentrated under reduced pressure, and purified by a column chromatograph, to obtain methyl 2-methyl-1-m-tolyl-1H-benzo[d]imidazole-5-carboxylate as a purple solid (436 mg, 86%).

The above compound (398 mg, 1.42 mmol) was dissolved in 8 mL of THF/H$_2$O3/1 mixture solution in the presence of lithium hydroxide monohydrate (300 mg, 7.10 mmol) and stirred at room temperature for 12 hours, and then concentrated under reduced pressure. The solid generated by applying an aqueous 1N HCl solution thereto was filtered, to obtain 2-methyl-1-m-tolyl-1H-benzo[d]imidazole-5-carboxylic acid as a purple solid (330 mg, 88%), which was used in the next reaction without a separate purification process.

[Step 4] Preparation of (2-methyl-1-m-tolyl-1H-benzo[d]imidazol-5-yl)(piperidin-1-yl)methanone (Compound 98)

The compound obtained in Step 3 (80.0 mg, 0.300 mmol) was dissolved in DMF, and then HOBT (81 mg, 0.6 mmol), TEA (126 uL, 1.2 mmol), and piperidine 28.1 mg (0.330 mmol) were added thereto. EDC hydrochloride (25 mg, 0.13 mmol) was put thereinto at 0° C., and then stirred at room temperature for 12 hours. The reacted mixture was diluted with ethyl acetate (32 mL), and then washed with water (32 mL). The organic layer was dried over anhydrous magnesium sulfate, followed by filtering and concentrating under reduced pressure, and then subjected to column chromatography (MC:MeOH=30:1), to obtain a target compound (79.4 mg, 79%).

$^1$H NMR (600 MHz, chloroform-d1) d=7.72 (m, 1H), 7.44 (t, J=7.2 Hz, 1H), 7.31 (d, J=7.8 Hz, 1H), 7.26 (dd, J=1.8 Hz, 8.4 Hz, 1H), 7.10-7.13 (m, 3H), 3.70 (br, 2H), 3.39 (br, 2H), 2.49 (s, 3H), 2.43 (s, 3H), 1.51-1.66 (br m, 6H)

In order to evaluate PAR-2 inhibitory efficacy of Compound 98 prepared in the Example 1, in vitro and in vivo experiments were conducted.

Evaluation of In Vitro Activity of PAR-2 Inhibitor

Test Example 1

Calcium Immobilization Assay

In order to evaluate PAR-2 inhibitory activity of the synthesized material, first, an assay system capable of measuring the change in concentration of calcium ions in a cell in real-time was constructed, and then an evaluation was conducted by using the assay system. PAR-2 is a kind of G-protein coupled receptor (GPCR). When the PAR-2 is activated in the cell, phospholipase C-b (PLC-b) was activated to cleave phosphatidylinositol 4,5-bisphosphate (PIP2) into inositol triphosphate (IP3) and diacyl glycerol (DAG). The IP3 generated herein promotes secretion of calcium ions in an endoplasmic reticulum (ER), calcium ion reservoir in the cell, resulting in increasing calcium ions in the cell. An in vitro screening assay system capable of searching materials that may suppress the increase in concentration of calcium ions in the cell due to activation of PAR-2 was constructed based on the existing search results. As a PAR-2 activator used in the experiment, activating peptide (AP) was used. As a reagent for detecting the concentration of calcium ions in the cell, the Calcium-4 assay kit by Molecular Probe Company was used. HCT-15, a PAR-2-overexpressed cell line, was used as a cell line used in the experiment. PAR-2 inhibitory candidate materials was treated for 5 minutes and then treated with the AP, and the change in fluorescence was observed for 2 minutes in real-time by using FlexStation II of Molecular Device Company.

The PAR-2 inhibitory activity of the synthesized material was evaluated by using such the protocol, and the assay profile of Compound 98 synthesized in Example 1 was shown in FIG. 1.

Test Example 2

β-Arrestin GPCR Assay

An in vitro assay protocol capable of detecting activation of PAR-2 was additively introduced besides the calcium immobilization assay, and activity of the selected material was measured. First, the PAR-2 inhibitory activity of Compound 98 was measured by using the PathHunter™ β-arrestin GPCR assay kit by DiscoveRx Company, capable of detecting accumulation of β-arrestin, which is an intercellular reaction material primarily generated by activation of PAR-2. As the measurement results, an IC50 value slightly different from the Calcium immobilization assay was observed (Table 1).

TABLE 1

Comparison between Calcium-4 assay result and β-arrestin assay result

| | IC50 (μM) | | |
|---|---|---|---|
| Compound | Calcium-4 | PathHunter ™ | CC50 (μM) |
| Compound 98 | 242.6 | 95.28 | >100 |

Test Example 3

Confocal Microscopy

In order to visually confirm activation of PAR-2, a cell line having the following structure was prepared referring to the existing reference documents, and activation of PAR-2 was observed by using a confocal microscopy. As a cell line, Kirsten Murine Sarcoma Virus transformed rat kidney epithelial cell (KNRK cell) was used, which is a cell line where, normally, PAR-2 is not expressed. In the KNRK cell, flag epitope was tagged to an N-terminal and Myc epitope was tagged to a C-terminal, so that a stable transfected cell was constructed. Flag and Myc of the thus prepared KNRK-PAR-2 cell line were subjected to double staining, and activation or non-activation of PAR-2 was observed by using the confocal microscopy ([trypsin]=1 μM, [SLIGKV(AP)]=100 μM). When the PAR-2 was not activated, Flag and Myc were double-stained and thus appears yellow in the merged image. However, when the PAR-2 was activated, Flag was separated away and thus a red image was shown.

As the results that the KNRK-PAR-2 cell line was simultaneously treated with a selected material, Compound 98, together with trypsin, activating peptide (SLIGKV) ([trypsin]=1 μM, [SLIGKV (activating peptide)]=100 μM, [Compound 98]=200 μM), an yellowish image was observed, and thus it was confirmed that the activation of PAR-2 was suppressed.

Evaluation of In Vivo Activity of PAR-2 Inhibitor

Test Example 4

Experiment on Recovery of Acute Skin Barrier

The recovery rate after acute skin barrier disruption was evaluated on a selected compound by using nude mice. Skins of both abdominal regions of each of 6-8 week aged nude mice (SKH-1) were subjected to repetitive tape stripping, so that transepidermal water loss reached a level of about 35~40 g/m$^2$/hr, and then, respective samples were applied thereto. The transepidermal water loss was measured by using the TEWameter (Courage & Khazaka, Germany) immediately before and after skin barrier disruption and 3 hours and 6 hours after application, and the recovery rate of transepidermal water loss was calculated as follows.

$$\% \text{ Recovery of } TEWL = \left(1 - \left(\frac{TEWL_a - TEWL_c}{TEWL_a - TEWL_b}\right)\right) \times 100$$

(wherein, $TEWL_a$ is TEWL value immediately after barrier disruption, $TEWL_b$ is TEWL value at the baseline, and $TEWL_c$ is TEWL value at the indicated time.)

Figure 3:
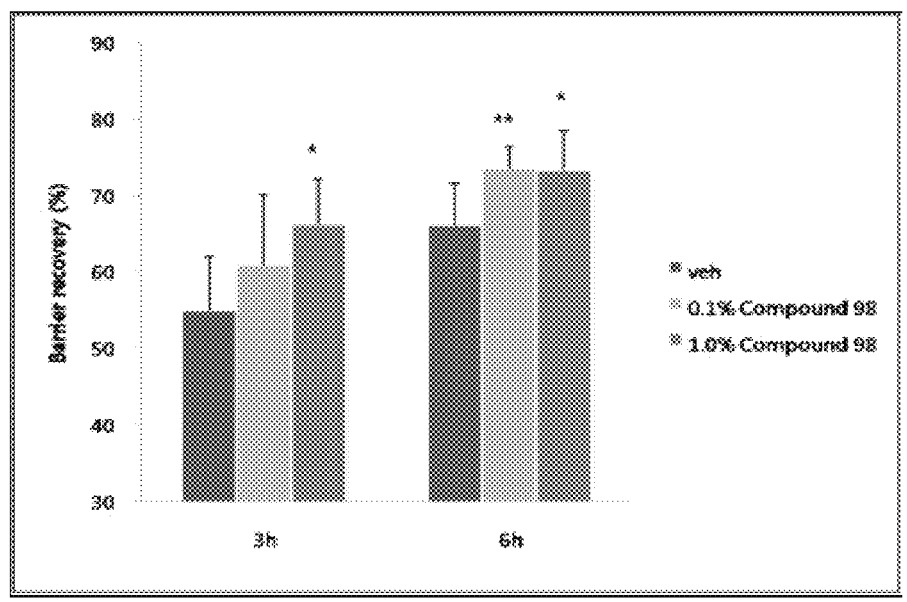
FIG. 3 shows effects of PAR-2 inhibitory candidate materials on the recovery after acute skin barrier disruption (**: $p<0.01$, *: $p<0.05$)

As the experiment results, the 1.0% Compound 98-treated group was observed to show rapid recovery. Also, the 0.1% Compound 98-treated group was observed to have a statistically significant difference. According to the existing research results, after the skin barrier disruption, activity of protease increased in epidermis of the disrupted region, which leads to an increase in activity of PAR-2 in the epidermis. It has been reported that the skin barrier is quickly disruption when activation of PAR-2 is suppressed, and the present study confirmed the same result that the PAR-2 inhibitor promotes skin barrier recovery. This study results showed through FIG. 3 that Compound 98 is a material having the best activity in promoting the recovery after skin barrier disruption.

Test Example 5

Oxazolone Model

Efficacy of a selected material was evaluated by using a chronic dermatitis animal model. An animal model of which chronic dermatitis was induced by continuously applying oxaozolone, which is a kind of hapten, to the nude mice was used. It has been reported that the recently developed oxazolone model showed various atopic dermatitis comparatively accurately, and the previous study conducted by the present inventors has confirmed that various symptoms of general atopic dermatitis are similar to clinical symptoms. In order to construct a chronic dermatitis animal model, 5% of oxazolone was applied to 6-week nude mice (SKH-1) and thus sensitized, and 0.1% of oxazolone was applied once every two days from a week after, resulting in inducing dermatitis symptom. The sample was applied to an animal after induction at an interval of once a day for three days, and various dermal functions and skin thickness change were observed. Finally, skin biopsy was conducted and histological observation was conducted.

As a positive control group used in the experiment, 0.05% of desonide, which is relatively low potency steroid, was used, and the transepidermal water loss, the moisture content in the stratum corneum, and skin thickness change were observed.

Figure 4:
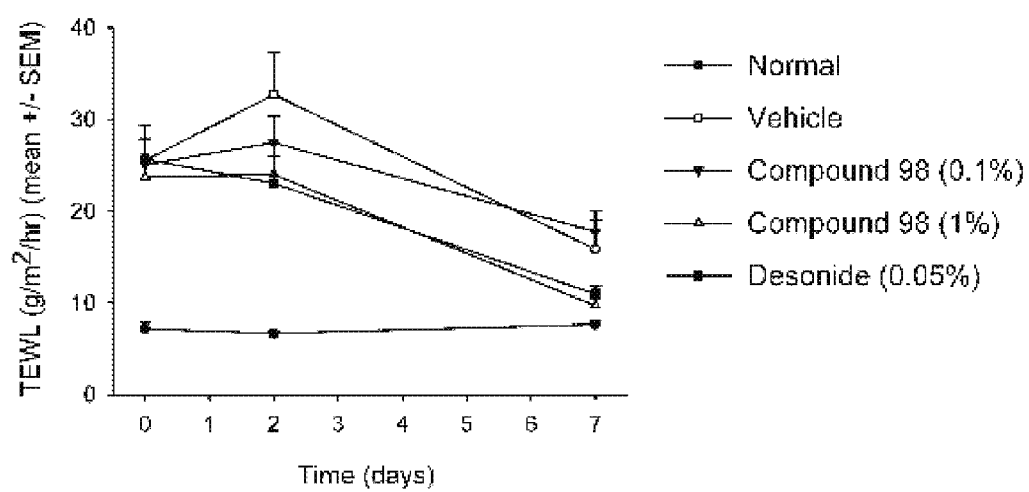
FIG. 4 shows changes in transdermal permeation loss by application of PAR-2 inhibitors in a chronic dermatitis animal model using oxazolone.
Figure 5:
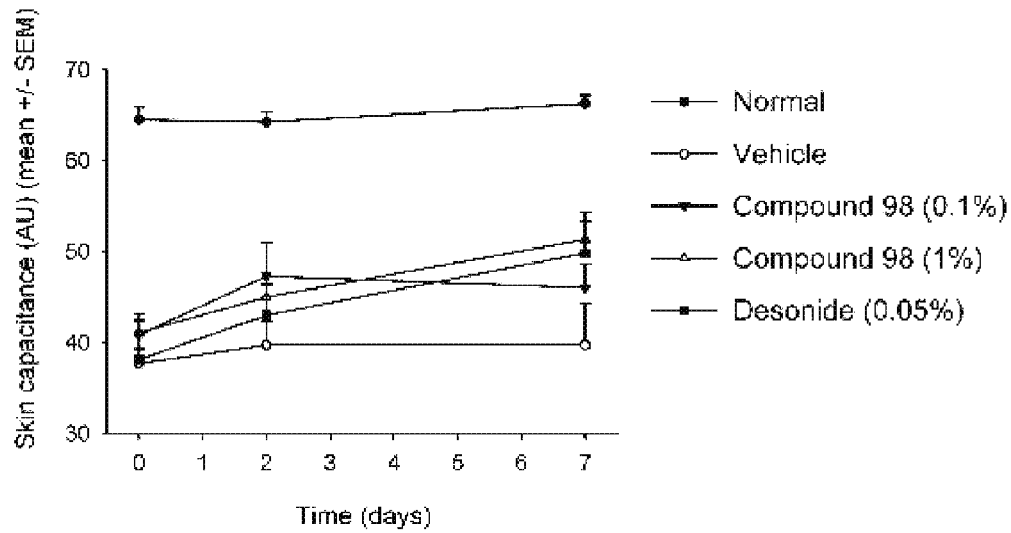
FIG. 5 shows changes in moisture content in stratum corneum by application of PAR-2 inhibitors in a chronic dermatitis animal model using oxazolone.

The results obtained by evaluating the inflammatory efficacy of Compound 98 using the oxazolone model are as follows. As for the recovery of transepidermal water loss and the recovery of moisture content in the stratum corneum, the Compound 98-treated group was observed to have promoted recovery as compared with the control group (FIGS. 4 and 5).

Figure 6:
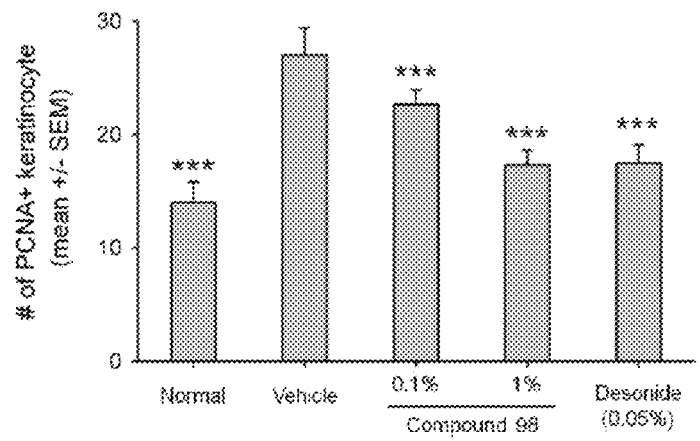
FIG. 6 shows changes in epidermal thickness by application of PAR-2 inhibitors in a chronic dermatitis animal model using oxazolone.
Figure 7:
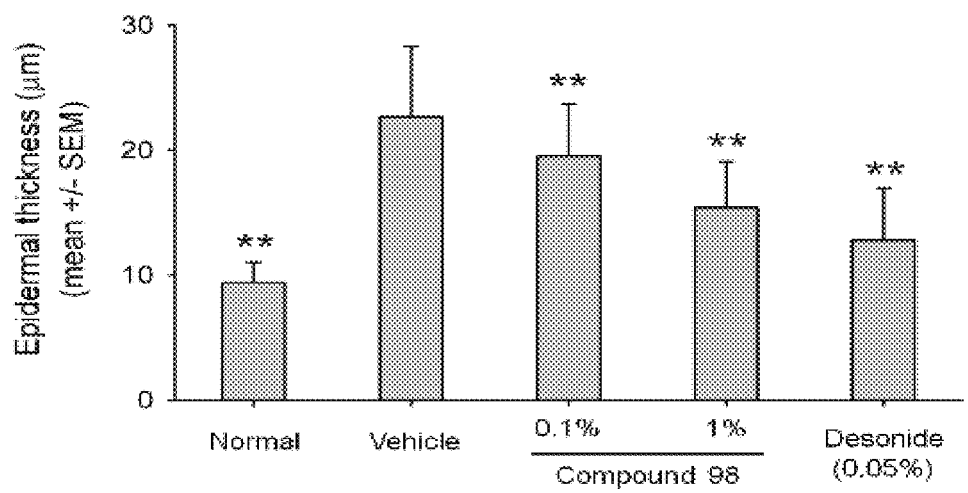
FIG. 7 shows effects on PCNA-positive keratinocyte, of selective materials in a chronic dermatitis animal model using oxazolone.

The tissue after treatment for 5 days was subjected to biopsy and H&E staining was performed, and thus the skin thickness change was measured. As the result, it was confirmed that all the treated groups had a statically significant decrease in skin thickness as compared with untreated groups (FIG. 6). As the PCNA staining results, it was observed that the Compound 98-treated group had a statically significant decrease in PCNA positive keratinocyte as compared with the control group (FIG. 7).

The invention claimed is:
1. A heterocyclic compound of Chemical Formula 2 below:

[Chemical Formula 2]

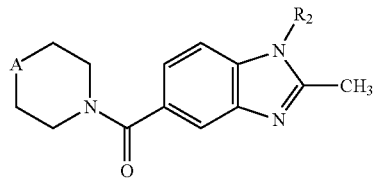

wherein A is $CH_2$ or $NR_{31}$;
$R_{31}$ is a (C3-C6)cycloalkylcarbonyl; and
$R_2$ is benzyl or phenyl, and the benzyl or phenyl of $R_2$ may be further substituted with halogen, (C1-C7)alkyl, or 5- or 6-membered heterocycloalkyl, or a pharmaceutically acceptable salt thereof.

2. The heterocyclic compound of claim 1, wherein the heterocyclic compound is selected from the group consisting of the following compounds:

Compound 93

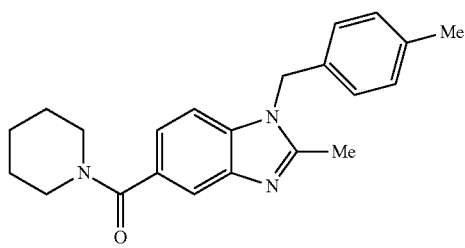

-continued

Compound 95

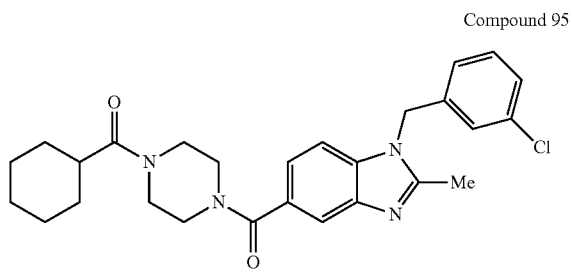

Compound 97

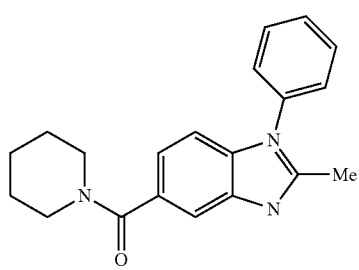

Compound 97

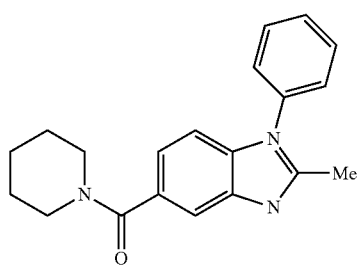

Compound 98

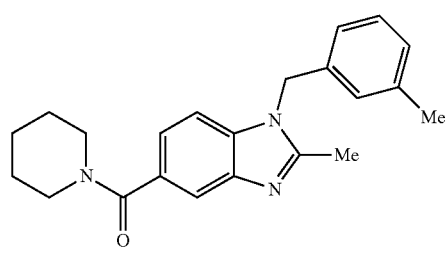

-continued

Compound 99

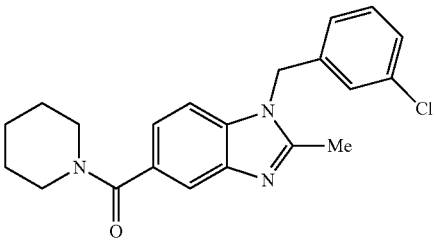

Compound 101 or a pharmaceutically acceptable salt thereof.

3. A pharmaceutical composition, comprising the heterocyclic compound or a pharmaceutically acceptable salt thereof according to claim 1 and a pharmaceutically acceptable carrier.

4. The pharmaceutical composition of claim 3, which is effective in treating acne, rosacea, seborrheic dermatitis, atopic dermatitis, post-inflammatory hyperpigmentation, contact dermatitis, pruritus, psoriasis, Lichen planus, eczema, skin infections, and Netherton Syndrome.

5. A method for treating skin wounds, comprising administering an effective amount of the heterocyclic compound or a pharmaceutically acceptable salt thereof according to claim 1 to a subject in need thereof.

6. A protease activated receptor 2 inhibitor composition comprising the heterocyclic compound or a pharmaceutically acceptable salt thereof according to claim 1.

7. A cosmetic composition comprising the heterocyclic compound or a pharmaceutically acceptable salt according to claim 1 and a cosmetically acceptable carrier.

8. A method for treating an inflammatory skin disease, comprising administering an effective amount of the heterocyclic compound or a pharmaceutically acceptable salt thereof according to claim 1 to a subject in need thereof.

9. The method of claim 8, wherein the inflammatory skin disease comprises acne, rosacea, seborrheic dermatitis, atopic dermatitis, post-inflammatory hyperpigmentation, contact dermatitis, pruritus, psoriasis, Lichen planus, eczema, skin infections, or Netherton Syndrome.

10. The method of claim 8, wherein the compound or a pharmaceutically acceptable salt thereof is administered orally, by injection, or by topical application to skin.

* * * * *